(12) United States Patent
Kmiecz et al.

(10) Patent No.: US 10,456,144 B2
(45) Date of Patent: Oct. 29, 2019

(54) BUR FOR DENTAL IMPLANTOLOGY

(75) Inventors: André Kmiecz, Mont-Soleil (CH);
Daniel Günter, Waldenburg (CH);
Marcello Memmolo, Sissach (CH)

(73) Assignee: STRAUMANN HOLDING AG, Basel (CH)

( * ) Notice: Subject to any disclaimer, the term of this patent is extended or adjusted under 35 U.S.C. 154(b) by 774 days.

(21) Appl. No.: 11/823,171

(22) Filed: Jun. 27, 2007

(65) Prior Publication Data
US 2007/0298376 A1 Dec. 27, 2007

(30) Foreign Application Priority Data

Jun. 27, 2006 (EP) .................................... 06116153

(51) Int. Cl.
*A61B 17/16* (2006.01)
*A61C 3/02* (2006.01)
*A61C 8/00* (2006.01)

(52) U.S. Cl.
CPC ............ *A61B 17/1615* (2013.01); *A61C 3/02* (2013.01); *A61C 8/0089* (2013.01); *A61B 17/1673* (2013.01)

(58) Field of Classification Search
CPC ..... A61C 3/02; A61C 17/1615; A61C 8/0089; B23B 51/02; A61B 17/32002; A61B 17/1617
USPC .................................... 433/165, 166; 606/80
See application file for complete search history.

(56) References Cited

U.S. PATENT DOCUMENTS

| 308,424 | A | * | 11/1884 | Morey .......................... 433/165 |
| 1,309,706 | A | * | 7/1919 | Taylor ........................... 408/230 |
| 4,190,958 | A | * | 3/1980 | Martin et al. ................. 433/102 |
| 5,017,137 | A | * | 5/1991 | Weissman ...................... 433/102 |
| 5,273,380 | A | * | 12/1993 | Musacchia .................... 408/230 |
| 5,387,059 | A | * | 2/1995 | Borzemsky ................... 433/165 |
| 5,791,902 | A | * | 8/1998 | Lauks ............................ 433/165 |
| 5,968,048 | A | * | 10/1999 | Harder ............................. 606/80 |
| 6,332,886 | B1 | * | 12/2001 | Green et al. .................... 606/80 |
| 6,902,400 | B1 | * | 6/2005 | Roetzer ......................... 433/165 |
| 2002/0031745 | A1 | * | 3/2002 | Kumar et al. ................. 433/165 |
| 2003/0211442 | A1 | * | 11/2003 | Abel .............................. 433/102 |
| 2004/0121283 | A1 | * | 6/2004 | Mason .......................... 433/102 |
| 2006/0111724 | A1 | * | 5/2006 | Yeung Wai Ping ............ 606/80 |
| 2006/0121415 | A1 | * | 6/2006 | Anitua Aldecoa ........... 433/165 |
| 2006/0210949 | A1 | | 9/2006 | Stoop |
| 2006/0228667 | A1 | * | 10/2006 | Buchanan ..................... 433/102 |
| 2007/0099150 | A1 | * | 5/2007 | Muller ..................... A61C 3/02 433/165 |
| 2007/0213736 | A1 | * | 9/2007 | Ducharme ...................... 606/80 |

FOREIGN PATENT DOCUMENTS

| DE | 1 883 930 | | 12/1963 |
| DE | 200 13 654 U1 | | 1/2001 |
| DE | 20 2004 000723 U1 | | 4/2004 |
| EP | 0765 640 A2 | | 4/1997 |
| GB | 2 405 365 A | | 3/2005 |
| WO | WO 2004/080325 A1 | | 9/2004 |
| WO | WO2005030418 A1 | * | 4/2005 ............. B23B 51/02 |

* cited by examiner

*Primary Examiner* — Heidi M Eide
(74) *Attorney, Agent, or Firm* — Scully, Scott, Murphy & Presser, P.C.

(57) ABSTRACT

A bur for dental implantology, including a dental coupling, a bur shank, a bur neck and a bur tip having at least one tip cutting edge, the tip cutting edge being partly rounded.

10 Claims, 1 Drawing Sheet

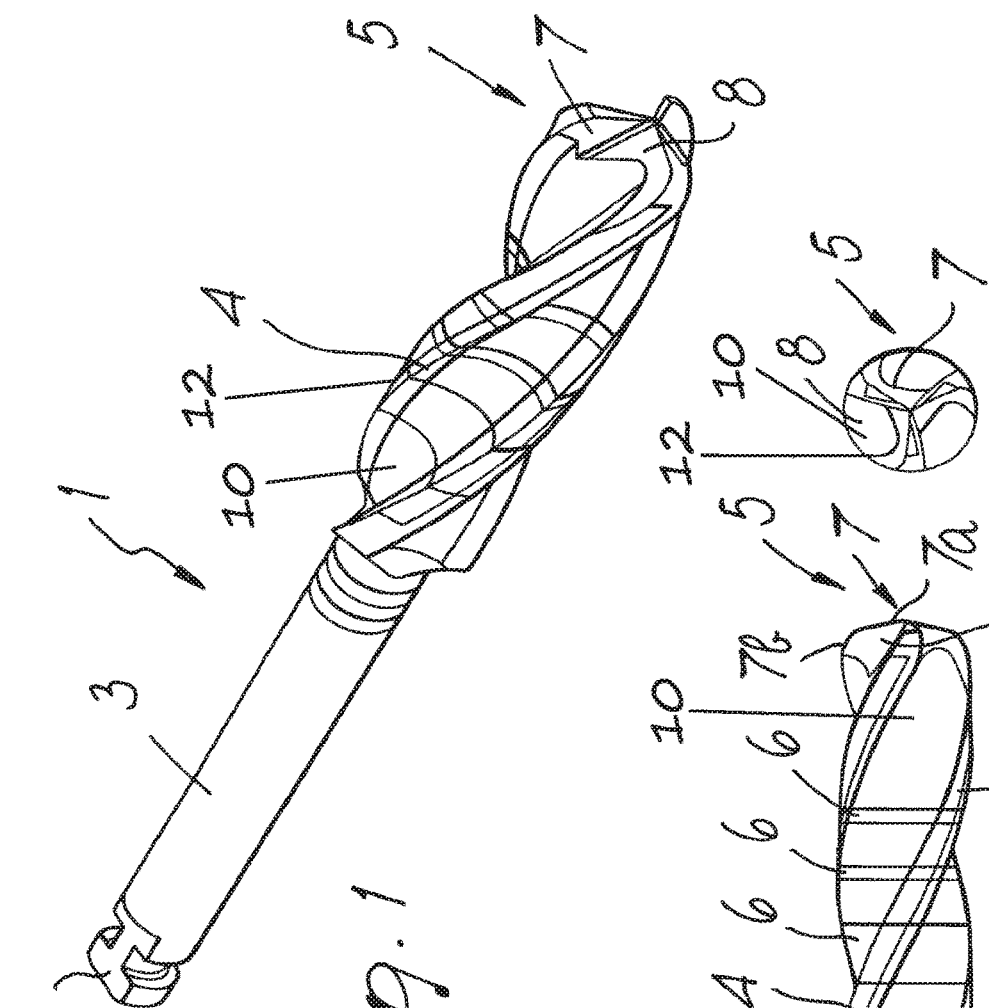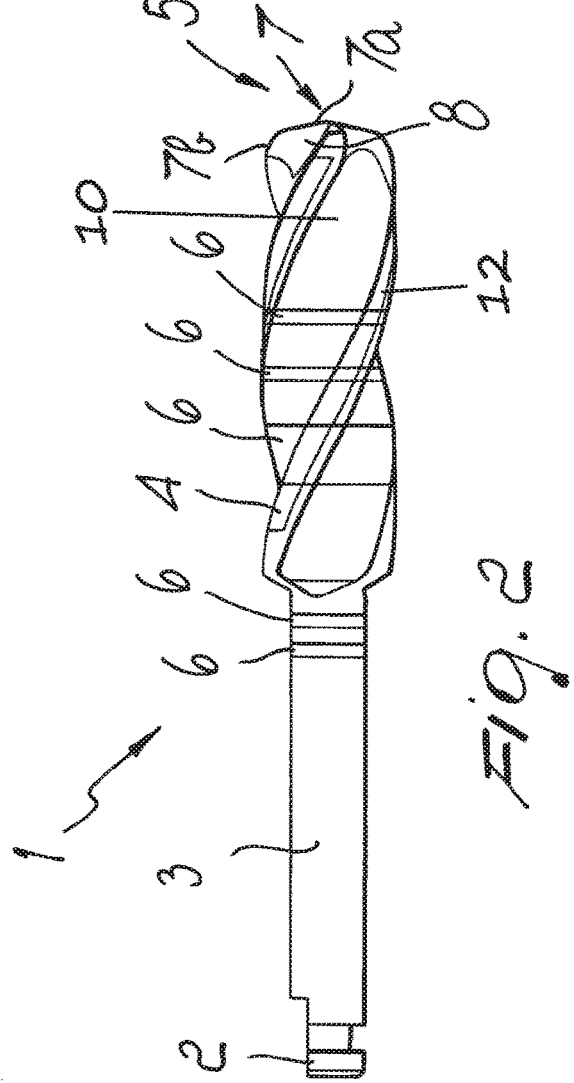

BUR FOR DENTAL IMPLANTOLOGY

The present invention relates generally to an improved bur for dental implantology and specifically to an improved bur for dental implantology which is suitable to simplify drilling of an existing bore.

BACKGROUND OF THE INVENTION

In dental implantology, it is well-known to use for the drilling of bores as implant beds, a set of drills comprising bud bur, pilot bur and helical bur. Such a set of burs is manufactured, for instance, by the company Institut Straumann AG, Basel, Switzerland.

In practice, the procedure in drilling a bore as an implant bed is as follows. First, the exposed bone surface is smoothed with a bud bur and the implant site is marked with the bud bur and possibly enlarged, bud burs with increasing diameters being used in the latter case. Subsequently, the implant bed is prepared with a suitable pilot bur for determining the bore axis. In a final step, the implant bed is then drilled to the final necessary width using a suitable helical bur.

With the above procedure, however, drilling with the helical bur causes a rattle or deflection due to the cutting edges of the helical bur engaging with or being caught in the edge of the former smaller bore. This leads to the above-mentioned rattle or deflection of the helical bur.

Up to this now, this problem was solved by slightly chamfering the edges of the smaller bore with a profiling cutter before drilling with the helical bur. This solution, however, has the disadvantage of requiring an additional tool, i.e. a profiling cutter, and a corresponding working step.

Accordingly, in case of renewed boring to a larger diameter, an additional profiling cutter and working step would be necessary.

An alternative to the above solution is offered by WO 2004/080325 A1, wherein a pilot guide with smaller diameter is integrated in the tip of the helical bur. The smaller diameter of the pilot guide corresponds to the diameter of the previous pilot bur or pilot bore, respectively, and is used for better guidance of the helical bur.

The alternative of WO 2004/080325 A1 is not satisfactory insofar as it ablates unnecessary bone material at the pilot guide, a superfluous blind hole being formed apically in the implant bed which is not necessary for receiving the dental implant and is detrimental to osteointegration and implant healing. This disadvantage can be remedied by an appropriate design of the bore length and by the provision of an additional bur for ablation of the bone tissue in the area of the pilot guide, but this leads, in turn, to the problem of an additional tool and an additional working step.

SUMMARY OF THE INVENTION

Therefore it is an object of the present invention to provide a bur for dental implantology which avoids the above disadvantages and allows drilling on the implant bed without additional tools and is free from rattling or deflection.

The and other objects which will better appear in the following specification are achieved by a bur for dental implantology according to the appended claims.

BRIEF DESCRIPTION OF THE DRAWINGS

Further characteristics and advantages of the invention will become better apparent from the description of a preferred but not exclusive embodiment of the bur for dental implantology according to the invention, illustrated by way of non-limiting example in the accompanying drawings, wherein:

FIG. 1 shows a perspective view of a bur for dental implantology according to the present invention;

FIG. 2 shows a side view of the bur for dental implantology according to the invention;

FIG. 3 shows a view of the tip of the bur for dental implantology according to the invention.

DESCRIPTION OF THE PREFERRED EMBODIMENTS

With reference to the Figures, a currently preferred embodiment of the bur 1 according to the invention is shown. This bur can be based on a helical bur of the company Institut Straumann AG, Basel, Switzerland, available in a 3.5 mm diameter version, short or long (art. no. 044.218/219) or in a 4.2 mm diameter version, short or long (art. no. 044.222/223).

The bur 1 is conventionally equipped with a dental coupling 2, a bur shank 3, a bur neck 4 with at least one helical groove 10 and a corresponding bevel 12, and a bur tip 5 with at least one tip cutting edge 7 and a corresponding ridge 8. Additionally, several markings 6 for indicating the drilling depth are provided on the bur 1 in a conventional manner.

According to the invention, the tip cutting edge 7 of the bur tip 5 is provided with roundings 7b and edges 7a, as can be seen from the side view in FIG. 2. The roundings 7b border on the bur neck 4 so that the point of contact of the roundings 7b with the bur neck 4 corresponds to the diameter of the bur 1. Thus, the edges 7a belong to an imaginary cone whose axis runs through the axis of the bur, and the roundings 7b are part of an imaginary sphere whose center is also located on the axis of the bur. Preferably, the imaginary cone is blunt.

The rounding 7a of bur neck 4 directly connects the straight edge 7a to the bevel 12.

The edges 7a preferably form an angle of about 140° to about 180° between them; more preferred of about 150° to about 170°, and most preferred of about 160°.

Preferably, the imaginary sphere formed by the roundings 7b, whose center lies on the axis of the bur, has a radius of about 1.5 mm in case of a 4.2 mm helical bur with the designation indicated above. The radius for a 3.5 mm helical bur is also about 1.5 mm.

The invention achieves the intended aim and objects, since a bur, specifically a helical bur for dental implantology is provided which, although it has no guide tip, runs very smoothly and can be centered well, avoiding the problem of deflection.

Also, an additional bur for removing the bone in the pilot guide area, which has not been drilled away so far, becomes unnecessary, unlike with the solution according to WO 2004/080325 A1. Moreover, the additional working step for using the additional bur is avoided.

Although the invention has been described in connection with a helical bur, the person skilled in the art will readily understand that the bur tip according to the invention can also be applied to a pilot bur, provided that the latter is used for re-drilling an existing bore; in such case, naturally, the same advantages will be obtained as those described in connection with a helical bur.

The disclosures in EPA 06116153.5 from which this application claims priority are incorporated herein by reference.

What is claimed is:

1. A bur for dental implantology, comprising:
a dental coupling,
a bur shank,
a bur neck comprising at least two helical grooves and at least two bevels extending the length of the bur neck, and
a bur tip comprising at least two tip cutting edges, wherein each tip cutting edge comprises a straight edge and a rounding,
wherein the straight edges of the at least two tip cutting edges are a part of an imaginary cone with an obtuse angle, the straight edges converging at a point that is the apex of the imaginary cone, the axis of the imaginary cone running through the axis of the bur, and the straight edges extending from the apex of the imaginary cone to the rounding, and
wherein the rounding consists of a convex transition which directly connects a respective straight edge to a respective bevel of the bur neck, the bur neck having a diameter greater than the bur shank.

2. The bur for dental implantology according to claim 1, wherein the rounding is a part of an imaginary sphere whose center is also located on the axis of the bur.

3. The bur for dental implantology according to claim 2, wherein the straight edges of the at least two tip cutting edges form an angle of 140° to 180° therebetween.

4. The bur for dental implantology according to claim 2, wherein the straight edges of the at least two tip cutting edges form an angle of 150° to 170° therebetween.

5. The bur for dental implantology according to claim 2, wherein the straight edges of the at least two tip cutting edges form an angle of 160° therebetween.

6. The bur for dental implantology according to claim 2, wherein the bur comprises a helical bur or a pilot bur.

7. The bur for dental implantology according to claim 1, wherein the straight edges of the at least two tip cutting edges form an angle of 140° to 180° therebetween.

8. The bur for dental implantology according to claim 1, wherein the straight edges of the at least two tip cutting edges form an angle of 150° to 170° therebetween.

9. The bur for dental implantology according to claim 1, wherein the straight edges of the at least two tip cutting edges form an angle of 160° therebetween.

10. The bur for dental implantology according to claim 1, wherein the bur comprises a helical bur or a pilot bur.

* * * * *